United States Patent
Mo et al.

(10) Patent No.: US 11,969,146 B2
(45) Date of Patent: Apr. 30, 2024

(54) SELF-LOCKING DEVICE OF ENDOSCOPE

(71) Applicant: HUNAN VATHIN MEDICAL INSTRUMENT CO., LTD., Xiangtan (CN)

(72) Inventors: Wenjun Mo, Xiangtan (CN); Xiaofeng Jia, Xiangtan (CN); Guanhua Zhou, Xiangtan (CN); Peng Tang, Xiangtan (CN)

(73) Assignee: HUNAN VATHIN MEDICAL INSTRUMENT CO., LTD., Xiangtan (CN)

( * ) Notice: Subject to any disclaimer, the term of this patent is extended or adjusted under 35 U.S.C. 154(b) by 161 days.

(21) Appl. No.: 17/633,497

(22) PCT Filed: May 11, 2020

(86) PCT No.: PCT/CN2020/089658
§ 371 (c)(1),
(2) Date: Feb. 7, 2022

(87) PCT Pub. No.: WO2021/022859
PCT Pub. Date: Feb. 11, 2021

(65) Prior Publication Data
US 2022/0287547 A1    Sep. 15, 2022

(30) Foreign Application Priority Data
Aug. 7, 2019 (CN) .......................... 201910726342.4

(51) Int. Cl.
*A61B 1/00* (2006.01)
*A61B 1/005* (2006.01)

(52) U.S. Cl.
CPC .............................. *A61B 1/00042* (2022.02)

(58) Field of Classification Search
CPC ............ A61B 1/000042; A61B 1/0052; A61B 1/00002; A61B 1/000066; A61M 25/0136
See application file for complete search history.

(56) References Cited

U.S. PATENT DOCUMENTS 10,617,283 B2 * 4/2020 Wang ................. A61B 1/00042
2010/0312055 A1   12/2010 Konstorum
(Continued)

FOREIGN PATENT DOCUMENTS

| CN | 103654693 A | 3/2014 |
| CN | 104523321 A | 4/2015 |

(Continued)

*Primary Examiner* — Anh Tuan T Nguyen
*Assistant Examiner* — Rynae E Boler
(74) *Attorney, Agent, or Firm* — Bayramoglu Law Offices LLC

(57) ABSTRACT

A self-locking device of an endoscope is provided. The endoscope includes a housing and a toggle assembly. The toggle assembly includes a toggle support, an elastic support and a toggle handle. The toggle handle is sleeved on the toggle support. An inner side of the toggle support is provided with a toggle lever and a friction piece. One end of the toggle lever is hinged to the toggle handle, and the other end of the toggle lever is not connected to the friction piece. The toggle lever has an L-shaped cross section, with a middle bend fixed to the toggle support. The toggle lever is hinged to the toggle support through a first pin. When being stressed, the toggle lever is rotatable around the first pin, so as to push the friction piece to move.

2 Claims, 4 Drawing Sheets

(56) References Cited

U.S. PATENT DOCUMENTS

2013/0012781 A1\* 1/2013 Kaneko ................ A61B 1/0057
600/148
2017/0325659 A1 11/2017 Wang et al.

FOREIGN PATENT DOCUMENTS

| CN | 109077696 A | 12/2018 |
| CN | 109381227 A | 2/2019 |
| CN | 110367907 A | 10/2019 |
| CN | 110432853 A | 11/2019 |
| EP | 0306723 A1 | 3/1989 |
| EP | 2437646 B1 | 10/2018 |

\* cited by examiner

SELF-LOCKING DEVICE OF ENDOSCOPE

CROSS REFERENCE TO THE RELATED APPLICATIONS

This application is the national phase entry of International Application No. PCT/CN2020/089658, filed on May 11, 2020, which is based upon and claims priority to Chinese Patent Application No. 201910726342.4, filed on Aug. 7, 2019, the entire contents of which are incorporated herein by reference.

TECHNICAL FIELD

The present invention relates to the technical field of endoscopes, and more particularly, to a self-locking device of an endoscope.

BACKGROUND

At present, endoscopes are widely used in the medical field. In experiments or operations, medical workers control the position of the lens of the endoscope in the human body through the toggle handle, but they often cannot let go of their hands that operate the toggle handle while observing the internal structure of the human body.

SUMMARY

The purpose of this part is to outline some aspects of the embodiments of the present invention and to briefly describe some preferred embodiments. Some simplification or omission may be made in this part as well as in the abstract of specification and the title of the disclosure of the present invention to avoid blurring the purposes of this part, the abstract of specification and the title of the disclosure, and such simplification or omission cannot be used to limit the scope of the present invention.

The present invention is provided in view of the problems as mentioned above and/or existing in the prior art.

An objective of the present invention is to provide a self-locking device of an endoscope.

To solve the above technical problem, the present invention adopts the following technical solution: a self-locking device of an endoscope. The endoscope includes: a housing, being provided outside the endoscope and hollow inside; and a toggle assembly, including a toggle support, an elastic support and a toggle handle, where the toggle handle is sleeved on the toggle support and is movable along a sleeving direction; a shaft of the toggle support passes through the housing and is connected to the elastic support on the other side; an inner side of the toggle support is provided with a toggle lever and a friction piece; one end of the toggle lever is hinged to the toggle handle, and the other end of the toggle lever is not connected to the friction piece; the toggle lever has an L-shaped cross section, with a middle bend fixed to the toggle support; the toggle lever is hinged to the toggle support through a first pin; and when being stressed, the toggle lever is rotatable around the first pin, so as to push the friction piece to move.

In a preferred solution of the self-locking device of an endoscope of the present invention, one end of the toggle lever may be provided with a fitting bump, and one end of the friction piece may be provided with a fitted bump; and a plane on which the fitting bump may be located may be opposite to a plane on which the fitted bump may be located, so that the fitting bump and the fitted bump are fit with each other.

In a preferred solution of the self-locking device of an endoscope of the present invention, the fitting bump and the fitted bump may respectively have smooth curved surfaces.

In a preferred solution of the self-locking device of an endoscope of the present invention, the toggle lever and the toggle handle may be hinged through a second pin; a connecting end of the toggle lever may be provided with a long oval hole; and the second pin may pass through the long oval hole to be fit with the toggle support.

In a preferred solution of the self-locking device of an endoscope of the present invention, one end of the friction piece may be fixed to the other end of the elastic support through a long shaft.

In a preferred solution of the self-locking device of an endoscope of the present invention, the number of the fitting bump may be identical to the number of the fitted bump.

The present invention has the following beneficial effects. The toggle handle is moved to drive the toggle lever to move along with the toggle handle, and the tail end of the toggle lever is in contact with the friction piece. The friction piece moves back and forth, such that the elastic support is close to and away from the housing, such that the self-locking of the toggle handle is realized through the contact between the friction piece and the tail end of the toggle lever. The self-locking of the endoscope is achieved by making the elastic support close to and away from the housing. The present invention features simple structure, low production cost and high work efficiency.

BRIEF DESCRIPTION OF THE DRAWINGS

To describe the technical solutions in the embodiments of the present invention more clearly, the following briefly describes the drawings required for describing the embodiments or the prior art. Apparently, the drawings in the following description show merely some of the embodiments of the present invention, and those of ordinary skill in the art may still derive other drawings from these drawings without creative efforts. Drawings.

DETAILED DESCRIPTION OF THE EMBODIMENTS

To make the above objectives, features and advantages of the present invention clearer, the specific implementations of the present invention are described in detail below with reference to the drawings of the specification.

Many specific details are set forth in the following description to facilitate full understanding of the present invention, but the present invention may also be implemented in other ways different from those described herein, similar derivatives may be made by those skilled in the art without departing from the connotation of the present invention, and therefore, the present invention is not limited by the specific embodiments disclosed below.

In addition, the "one embodiment" or "embodiments" herein refers to a particular feature, structure or characteristic that may be included in at least one implementation of the present invention. The "in one embodiment" appearing in different places in the specification does not refer to the same embodiment, nor is it a separate or selective embodiment mutually exclusive with other embodiments.

Figure 1:
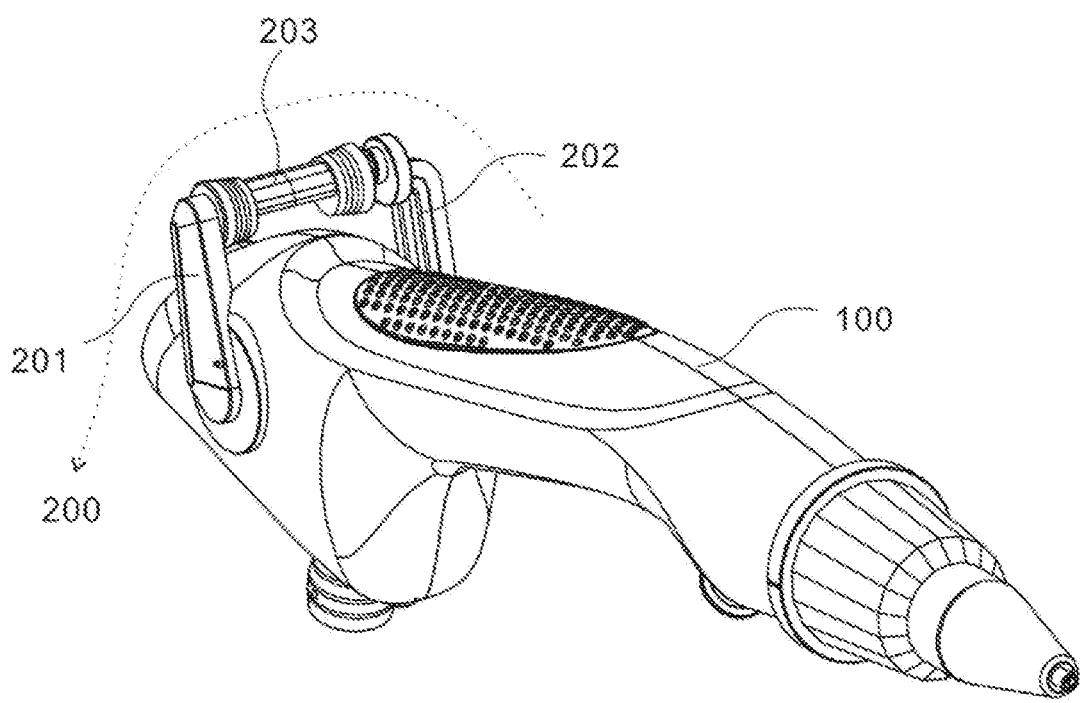
FIG. 1 is a full structural view of a self-locking device of an endoscope according to an embodiment of the present invention.
Figure 2:
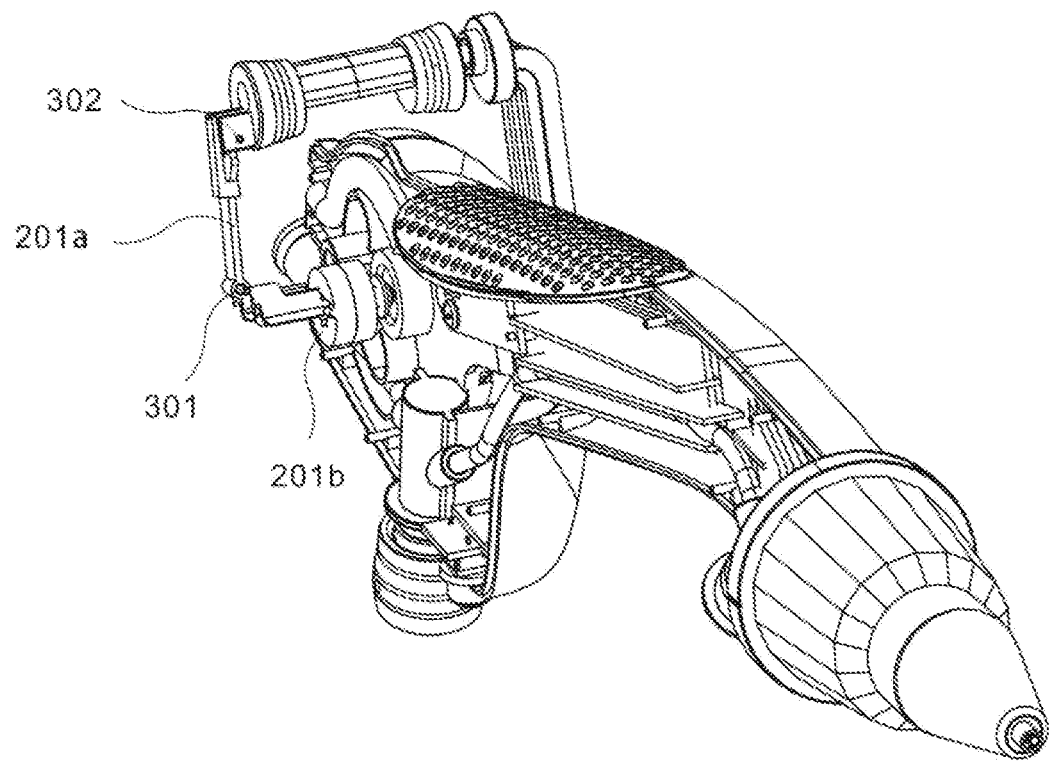
FIG. 2 is a full structural view of the self-locking device of an endoscope with a housing removed according to an embodiment of the present invention.
Figure 3:
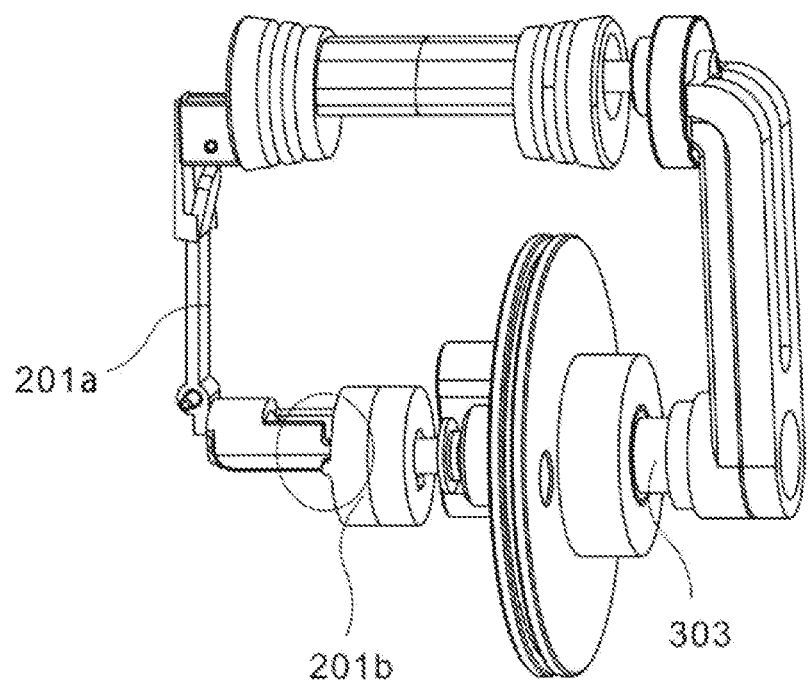
FIG. 3 is a partial structural view of the self-locking device of an endoscope according to an embodiment of the present invention.
Figure 4:
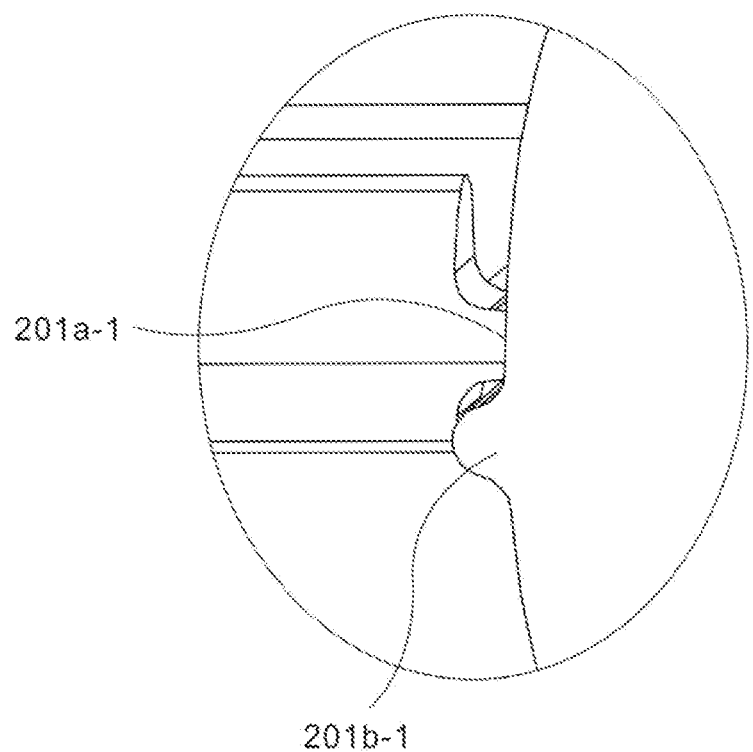
FIG. 4 is a detail view of FIG. 3 of the self-locking device of an endoscope according to an embodiment of the present invention.
Figure 5:
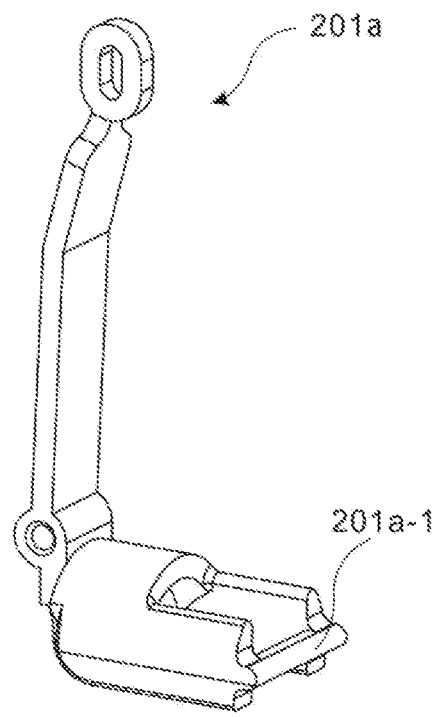
FIG. 5 is a full structural view of a toggle lever of the self-locking device of an endoscope according to an embodiment of the present invention.

Referring to FIGS. 1 to 5, a first embodiment of the present invention provides a self-locking device of an endoscope. In this embodiment, the endoscope includes a housing 100 and a toggle assembly 200. The toggle assembly 200 is located outside the housing 100 and performs relative rotational motion.

The housing 100 is provided outside the endoscope. The housing 100 is hollow inside to accommodate internal components and cords of the endoscope.

The toggle assembly 200 includes a toggle support 201, an elastic support 202 and a toggle handle 203. The toggle handle 203 is sleeved on the toggle support 201 and is movable along a sleeving direction. A shaft of the toggle support 201 passes through the housing 100 and is connected to the elastic support 202 on the other side. That is to say, the toggle handle 203 is sleeved on the toggle support 201, and it is movable left and right along the toggle support 201.

An inner side of the toggle support 201 is provided with a toggle lever 201a and a friction piece 201b. The toggle lever 201a has an L-shaped cross section, with a middle bend fixed to the toggle support 201. The toggle lever 201a is hinged to the toggle support 201 through a first pin 301. When being stressed, the toggle lever 201a is rotatable around the first pin 301, so as to push the friction piece 201b to move.

It should be noted that the toggle lever 201a and the toggle handle 203 are hinged through a second pin 302, a connecting end of the toggle lever 201a is provided with a long oval hole, and the toggle handle 203 passes through the long oval hole to be fit with the toggle support 201. Therefore, when the toggle handle 203 moves on the toggle support 201, the toggle lever 201a provided with the long oval hole is movable up and down and left and right around the second pin 302. The left-right direction is perpendicular to the toggle support 201.

It should be noted that, in this embodiment, there is no connection between the friction piece 201b and the toggle lever 201a.

Preferably, one end of the toggle lever 201a is provided with a fitting bump 201a-1, and one end of the friction piece 201b is provided with a fitted bump 201b-1. A plane on which the fitting bump 201a-1 is located is opposite to a plane on which the fitted bump 201b-1 is located, so that the fitting bump and the fitted bump are fit with each other.

Preferably, the fitting bump 201a-1 and the fitted bump 201b-1 respectively have smooth curved surfaces. For example, the fitting bump 201a-1 and the fitted bump 201b-1 have semicircular cross sections.

Preferably, the number of the fitting bump 201a-1 is identical to the number of the fitted bump 201b-1.

In the present invention, a working principle of the self-locking device of the endoscope is as follows. In an initial state, the toggle handle 203 is placed on a left side of the toggle support 201. The toggle handle 203 is manually toggled to move from the left side of the toggle support 201 to a right side of the toggle support 201, and it stays at the right side of the toggle support 201. When the toggle handle 203 moves from the left side of the toggle support 201 to the right side of the toggle support 201, one end of the long oval hole of the toggle lever 201a moves relative to the second pin 302, such that the toggle lever 201a rotates around the first pin 301. As shown in the figure, in an initial position, the fitting bump 201a-1 is placed under the fitted bump 201b-1. When the toggle lever 201a rotates around the first pin 301, the fitting bump 201a-1 is placed above the fitted bump 201b-1.

Referring to FIGS. 1 to 5, a second embodiment of the present invention provides a self-locking device of an endoscope. Different from the first embodiment, in the second embodiment, one end of the friction piece 201b is fixed to the other end of the elastic support 202 through a long shaft 303.

Specifically, in this embodiment, the endoscope includes a housing 100 and a toggle assembly 200. The toggle assembly 200 is located outside the housing 100 and performs relative rotational motion.

The housing 100 is provided outside the endoscope. The housing 100 is hollow inside to accommodate internal components and cords of the endoscope.

The toggle assembly 200 includes a toggle support 201, an elastic support 202 and a toggle handle 203. The toggle handle 203 is sleeved on the toggle support 201 and is movable along a sleeving direction. A shaft of the toggle support 201 passes through the housing 100 and is connected to the elastic support 202 on the other side. That is to say, the toggle handle 203 is sleeved on the toggle support 201, and it is movable left and right along the toggle support 201.

An inner side of the toggle support 201 is provided with a toggle lever 201a and a friction piece 201b. The toggle lever 201a has an L-shaped cross section, with a middle bend fixed to the toggle support 201. The toggle lever 201a is hinged to the toggle support 201 through a first pin 301. When being stressed, the toggle lever 201a is rotatable around the first pin 301, so as to push the friction piece 201b to move.

It should be noted that the toggle lever 201a and the toggle handle 203 are hinged through a second pin 302, a connecting end of the toggle lever 201a is provided with a long oval hole, and the toggle handle 203 passes through the long oval hole to be fit with the toggle support 201. Therefore, when the toggle handle 203 moves on the toggle support 201, the toggle lever 201a provided with the long oval hole is movable up and down and left and right around the second pin 302. The left-right direction is perpendicular to the toggle support 201.

It should be noted that, in this embodiment, there is no connection between the friction piece 201b and the toggle lever 201a.

Preferably, one end of the toggle lever 201a is provided with a fitting bump 201a-1, and one end of the friction piece 201b is provided with a fitted bump 201b-1. A plane on which the fitting bump 201a-1 is located is opposite to a plane on which the fitted bump 201b-1 is located, so that the fitting bump and the fitted bump are fit with each other.

Preferably, the fitting bump 201a-1 and the fitted bump 201b-1 respectively have smooth curved surfaces. For example, the fitting bump 201a-1 and the fitted bump 201b-1 have semicircular cross sections.

Preferably, the number of the fitting bump 201a-1 is identical to the number of the fitted bump 201b-1.

In the present invention, a working principle of the self-locking device of the endoscope is as follows. In an initial state, the toggle handle 203 is placed on a left side of the toggle support 201. The toggle handle 203 is manually toggled to move from the left side of the toggle support 201 to a right side of the toggle support 201, and it stays at the right side of the toggle support 201. When the toggle handle 203 moves from the left side of the toggle support 201 to the right side of the toggle support 201, one end of the long oval hole of the toggle lever 201a moves relative to the second pin 302, such that the toggle lever 201a rotates around the first pin 301. As shown in the figure, in an initial position, the fitting bump 201a-1 is placed under the fitted bump 201b-1. When the toggle lever 201a rotates around the first pin 301, the fitting bump 201a-1 is placed above the fitted bump 201b-1.

It should be noted that, one end of the friction piece 201b is fixed to the other end of the elastic support 202 through the long shaft 303. During a whole movement process, in the initial state, the elastic support 202 is in contact with the housing 100, so the resistance of pulling a tail end of a cord through the toggle assembly 200 is very large. The tail end of the cord is self-locking without external force, and it is difficult to be pulled by the toggle assembly 200. When the fitting bump 201a-1 moves from below the fitted bump 201b-1 to above the fitted bump 201b-1, the friction piece 201b pushes the long shaft 303 such that the elastic support 202 does not contact the housing 100. In this way, the resistance of pulling the tail end of the cord through the toggle assembly 200 is reduced, such that the tail end of the cord can move freely through the toggle assembly 200.

Figure 6:
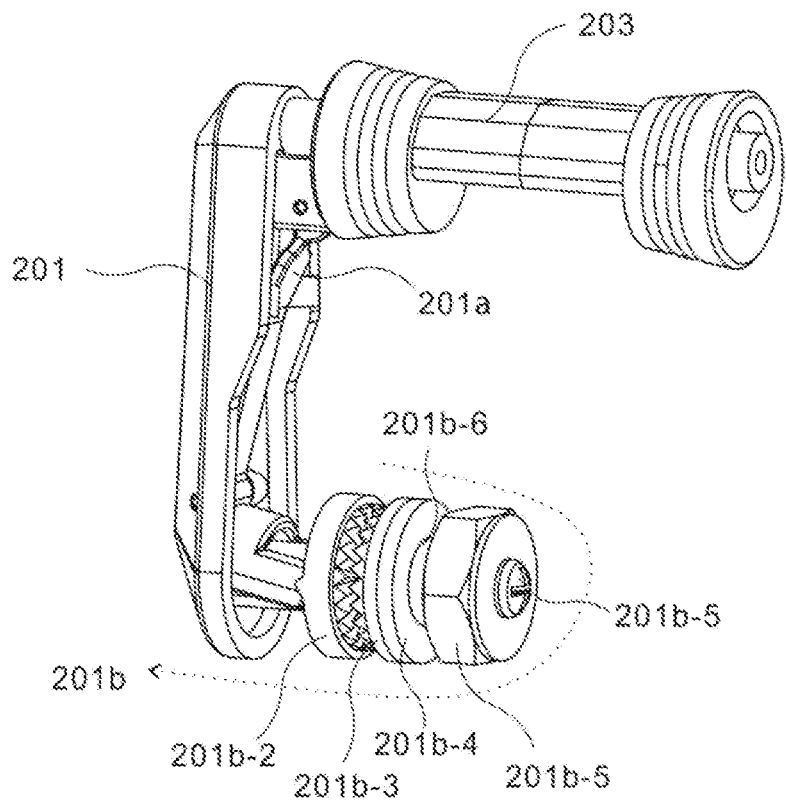
FIG. 6 is a partial structural view of the toggle lever of the self-locking device of an endoscope according to an embodiment of the present invention.
Figure 7:
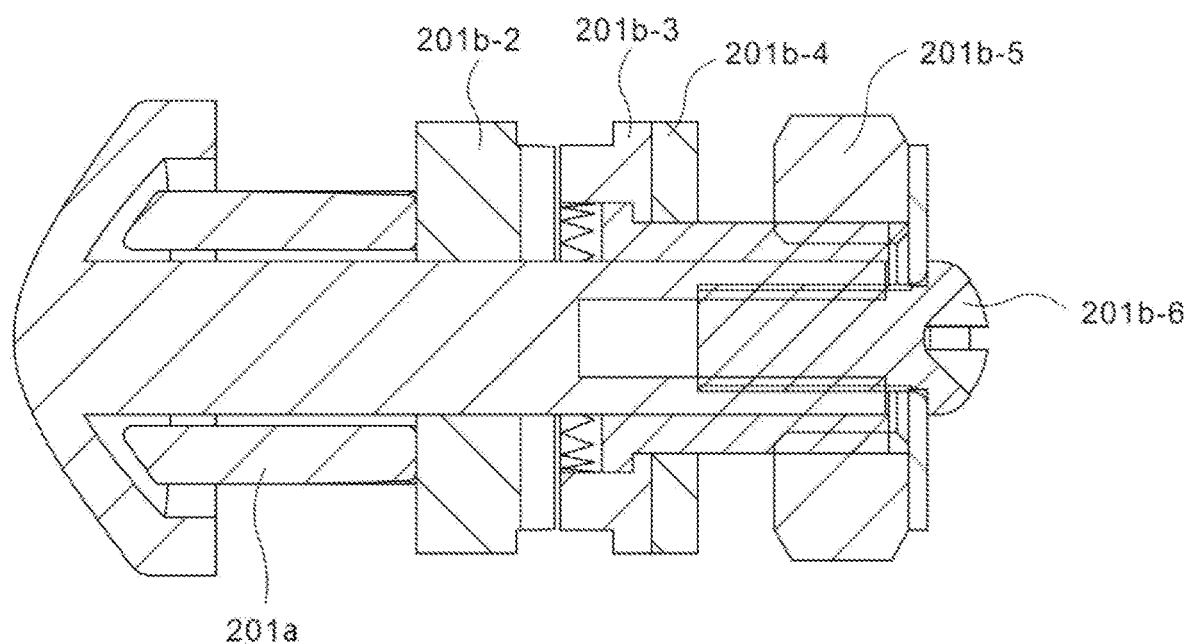
FIG. 7 is a partial sectional view of a friction piece, shown in FIG. 6, of the self-locking device of an endoscope according to an embodiment of the present invention.

Referring to FIGS. 1 to 7, another embodiment of the present invention provides a self-locking device of an endoscope. In this embodiment, the friction piece 201b includes a first gear 201b-2, a second gear 201b-3, a rubber sheet 201b-4, a nut 201b-5 and a bolt 201b-6. In the toggle support 201, the bolt 201b-6 passes through the second gear 201b-3 and the rubber sheet 201b-4, and is fixed to the nut 201b-5 at the other end.

It should be noted that, in this embodiment, a spring is provided between the first gear 201b-2 and the second gear 201b-3, such that the first gear 201b-2 and the second gear 201b-3 can be reset without external force.

It should be noted that the fitted bump 201b-1 is provided on the first gear 201b-2.

In this embodiment, a working principle of the self-locking device of the endoscope is as follows. In an initial state, the toggle handle 203 is placed on a left side of the toggle support 201. The toggle handle 203 is manually toggled to move from the left side of the toggle support 201 to a right side of the toggle support 201, and it stays at the right side of the toggle support 201. When the toggle handle 203 moves from the left side of the toggle support 201 to the right side of the toggle support 201, one end of the long oval hole of the toggle lever 201a moves relative to the second pin 302, such that the toggle lever 201a rotates around the first pin 301. As shown in the figure, in an initial position, the fitting bump 201a-1 is placed under the fitted bump 201b-1. When the toggle lever 201a rotates around the first pin 301, the fitting bump 201a-1 is placed above the fitted bump 201b-1. At this time, the first gear 201b-2 meshes with the second gear 201b-3, and the tightness is adjusted by adjusting a gap between the nut 201b-5 and the housing 100.

During the entire movement process, in the initial state, the first gear 201b-2 meshes with the second gear 201b-3, and the adjusting nut 201b-5 is in close contact with the housing 100. Thus, the resistance of pulling a tail end of a cord through the toggle assembly 200 is very large. The tail end of the cord is self-locking without external force, and it is difficult to be pulled by the toggle assembly 200. When the adjusting nut 201b-5 is in loose contact with the housing 100, the resistance of the toggle assembly 200 to pull the tail end of the cord is reduced, and the toggle assembly 200 can easily pull the tail end of the cord.

It is important to note that the configurations and arrangements of the present invention shown in the various exemplary implementation schemes are merely illustrative. Although only a few implementation schemes are described in detail in the present invention, it should be readily understood by those referring to the disclosure that many modifications (such as the sizes, dimensions, structures, shapes, ratios, parameter values, mounting arrangements, material use, colors and orientation changes of various elements) are possibly made without departing from the novel teachings and advantages of the subject matter described in the present invention. For example, an element shown as integrally formed may be composed of multiple parts or elements, the position of the element may be reversed or otherwise altered, and the nature or number or location of the discrete elements may be altered. Accordingly, all such modifications are intended to be included within the scope of the present invention. The order or sequence of any process or method steps may be changed or re-sequenced according to alternative implementation schemes. Other substitutions, modifications, changes and omissions may be made in the design, operation and arrangement of the exemplary implementation schemes without departing from the scope of the present invention. Therefore, the present invention is not limited to a specific implementation scheme, but extends to various modifications that come within the scope of the appended claims.

In addition, for a concise description of the exemplary implementation schemes, all features of actual implementation schemes (i.e., those that are not related to the currently considered best mode for carrying out the present invention, or those that are not related to the practice of the present invention) may not be described.

It should be understood that a large number of specific implementation decisions may be made in the development of any actual implementation, such as in any engineering or design project. Such development efforts may be complex and time-consuming, but for those of ordinary skill who benefit from this disclosure, they do not need too many experiments, and such development efforts will be a routine work of design, manufacturing and production.

It should be noted that the above embodiments are only intended to explain, rather than to limit the technical solutions of the present invention. Although the present invention is described in detail with reference to the preferred embodiments, those skilled in the art should understand that modifications or equivalent substitutions may be made to the technical solutions of the present invention without departing from the spirit and scope of the technical solutions of the present invention, and such modifications or equivalent substitutions should be included within the scope of the claims of the present invention.

What is claimed is:

1. A self-locking device of an endoscope, wherein the self-locking device comprises:
   a housing; and
   a toggle assembly, comprising a toggle support, an elastic support and a toggle handle, wherein
   the toggle handle is connected to the toggle support; and
   a shaft of the toggle support passes through the housing, and the shaft of the toggle support is connected to a first end of the elastic support;
   wherein the toggle support is provided with a toggle lever and a friction piece; and a first end of the toggle lever is hinged to the toggle handle;
   the toggle lever has an L-shaped cross section; the toggle lever is hinged to the toggle support through a first pin; and the toggle lever is rotatable around the first pin to push the friction piece to move; and
   a second end of the toggle lever is provided with a fitting bump, and a first end of the friction piece is provided with a fitted bump; and the fitting bump and the fitted bump are fit with each other;
   wherein the fitting bump and the fitted bump each have smooth curved surfaces; and
   wherein the first end of the toggle lever and the toggle handle are hinged through a second pin; the first end of the toggle lever is provided with a long oval hole, wherein the first end of the toggle lever is a connecting end; and the second pin passes through the long oval hole to be fit with the toggle support.

2. The self-locking device of the endoscope according to claim 1, wherein a number of the fitting bump on the second end of the toggle lever is identical to a number of the fitted bump on the first end of the friction piece.

* * * * *